(12) United States Patent
Cottens et al.

(10) Patent No.: US 7,205,279 B2
(45) Date of Patent: *Apr. 17, 2007

(54) PHARMACEUTICAL COMPOSITIONS

(75) Inventors: Sylvain Cottens, Witterswil (CH); Barbara Haeberlin, Riehen (CH); Richard Sedrani, Basel (CH); Jacky Vonderscher, Riedisheim (FR)

(73) Assignee: Novartis AG, Basel (CH)

( * ) Notice: Subject to any disclaimer, the term of this patent is extended or adjusted under 35 U.S.C. 154(b) by 1033 days.

This patent is subject to a terminal disclaimer.

(21) Appl. No.: 09/738,104

(22) Filed: Dec. 15, 2000

(65) Prior Publication Data

US 2004/0006012 A1  Jan. 8, 2004

Related U.S. Application Data

(63) Continuation of application No. 09/688,677, filed on Sep. 22, 2000, now abandoned, which is a continuation of application No. 08/737,774, filed as application No. PCT/EP95/04187 on Oct. 25, 1995.

(51) Int. Cl.
*A61K 9/66* (2006.01)
*A61K 38/00* (2006.01)

(52) U.S. Cl. .............. 514/11; 514/9; 514/937; 514/938; 514/970; 514/975; 424/455

(58) Field of Classification Search ............... 424/400, 424/450, 452, 455; 514/11, 937, 938, 970, 514/975, 9
See application file for complete search history.

(56) References Cited

U.S. PATENT DOCUMENTS

| 5,476,843 | A |   | 12/1995 | Wohlrab et al. |         |
|-----------|---|---|---------|----------------|---------|
| 5,603,951 | A | * | 2/1997  | Woo            | 424/455 |
| 5,639,474 | A | * | 6/1997  | Woo            | 424/452 |
| 5,932,243 | A | * | 8/1999  | Fricker et al. | 424/450 |
| 5,985,321 | A | * | 11/1999 | Brox et al.    | 424/451 |

* cited by examiner

*Primary Examiner*—Elli Peselev
(74) *Attorney, Agent, or Firm*—Thomas R. Savitsky

(57) ABSTRACT

This invention provides a microemulsion pre-concentrate comprising a difficultly soluble active agent and a carrier medium comprising 1) a hydrophilic phase which comprises dimethylisosorbide and/or a lower alkyl alkanoic ester, 2) a lipophilic phase, and 3) a surfactant. The active agent may be a cyclosporin or a macrolide.

Figure 1:
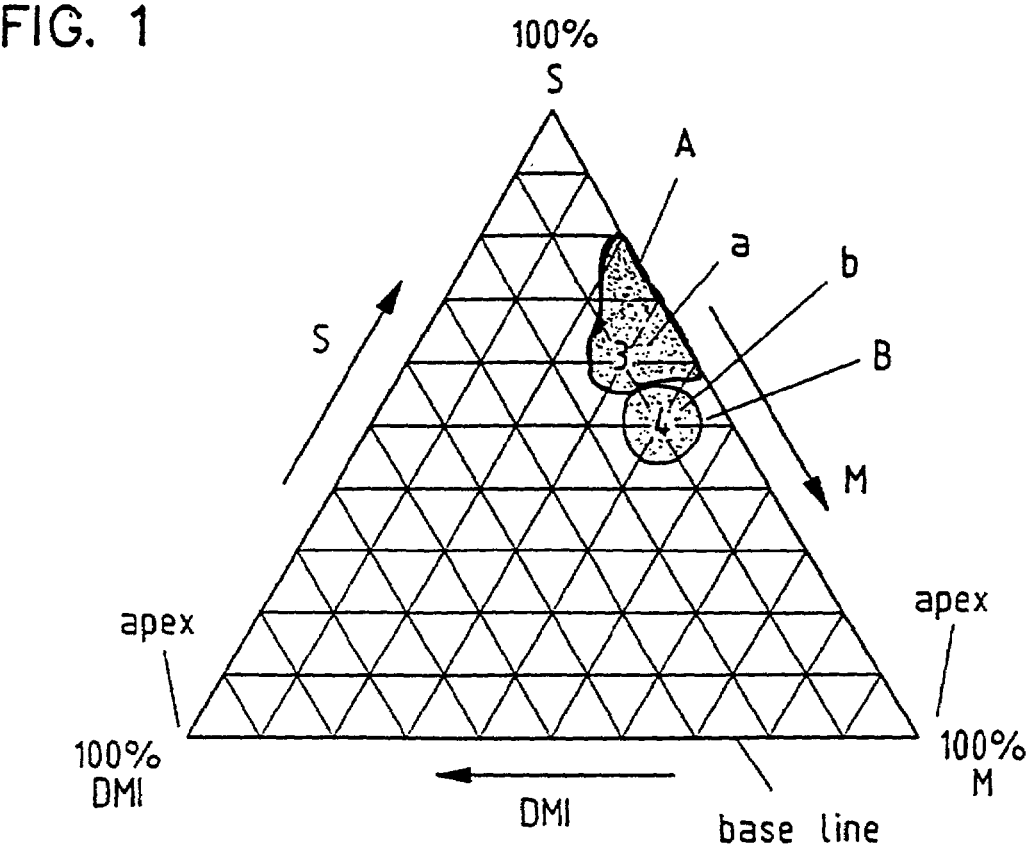

In another aspect, this invention provides a pharmaceutical composition for enteral or parenteral administration comprising a macrolide and an acid.

4 Claims, 3 Drawing Sheets

PHARMACEUTICAL COMPOSITIONS

This application is a continuation of U.S. Ser. No. 09/668,677, filed Sep. 22, 2000, abandoned, which was a continuation of U.S. Ser. No. 08/737,774, filed Nov. 25, 1996, abandoned, which was a 371 application of PCT/EP95/04187, having an international filing date of Oct. 25, 1995.

The present invention relates to novel galenic compositions, in particular novel galenic compositions in which the active ingredient is a difficultly soluble active agent e.g. a macrolide, or in particular a cyclic poly-N-methylated undecapeptide or peptolide of the cyclosporin class—see e.g. GB patent publications nos. 2 222 770 and 2 257 359 A and equivalents world-wide.

As discussed in the said GB patent publications, the cyclosporins present highly specific difficulties in relation to administration generally and galenic composition in particular, including in particular problems of stability, drug bioavailability, and variability in inter- and intra-patient dose response.

In order to meet these and related difficulties, in GB patent publication no. 2 222 770 and 2 257 359 A, galenic compositions are disclosed comprising a cyclosporin as active ingredient and which take the form of, inter alia, a microemulsion or microemulsion pre-concentrate. Such compositions typically comprise 1) a hydrophilic phase, 2) a lipophilic phase, and 3) a surfactant.

In accordance with the present invention it has now surprisingly been found that particularly stable microemulsion or microemulsion pre-concentrate galenic compositions with difficultly soluble active agents having particularly interesting bioavailability characteristics and reduced variability in inter- and intra-subject bioavailability parameters, are obtainable using a hydrophilic phase comprising dimethylisosorbide.

Dimethylisosorbide has been proposed in WO 94/05312 for use in the production of cyclosporin-containing compositions but only in the form of complex compositions. The scope of components of these compositions contemplated are precisely specified so it is clear that the applicants of WO 94/05312 believed that only few compositions based on dimethylisosorbide would work. Thus Examples 1, 2 and 6 of WO 94/05312 describe a composition containing dimethylisosorbide with the emulsifier anhydromannitol oleyl ether, (Montanide 103), another emulsifier, citroglyceride (Axol C62) and a lipogel aluminum magnesium hydroxy stearate (Gilugel MIG), and a short chain fatty acid glyceride (Miglyol 812) or milk thistle oil. Dimethylisosorbide is merely disclosed as a solvent and there is no hint that it could be used as a microemulsion hydrophilic phase component. The applicants of WO 94/05312 have failed to recognize its utility in this regard.

In accordance with the present invention, it has surprisingly been found that such microemulsion systems can, in contrast to the teaching of the art, in practice indeed be prepared comprising dimethylisosorbide as hydrophilic phase component.

The present invention provides in one aspect a pharmaceutical composition which is a microemulsion pre-concentrate comprising a difficultly soluble active agent and a carrier medium comprising 1) a hydrophilic phase which comprises dimethylisosorbide and/or a lower alkyl alkanoic ester,
2) a lipophilic phase, and
3) a surfactant.

Preferably the composition is in the form of a "microemulsion preconcentrate" of the type providing o/w (oil-in-water) microemulsions. However the composition may be in the form of a microemulsion which additionally contains an aqueous phase; preferably water.

A "microemulsion preconcentrate" is defined in this specification as being a composition which spontaneously forms a microemulsion in an aqueous medium, for example, in water, for example on dilution of 1:1 to 1:10, or in the gastric juices after oral application.

A "microemulsion" is a non-opaque or substantially non-opaque colloidal dispersion that is formed spontaneously or substantially spontaneously-when its components are brought into contact. A microemulsion is thermodynamically stable and contains dispersed particles of a size less than about 2000 Å. Generally microemulsions comprise droplets or particles having a mean diameter of less than about 1500 Å; typically less than 100 nm, generally greater than 10 nm, and stable over periods in excess of 24 hours. Further characteristics can be found in the above mentioned British patent application 2 222 770, the disclosure of which is incorporated herein by reference.

The lipophilic phase may comprise 5 to 85% by weight of the carrier medium, e.g. 10 to 85%; preferably 15 to 70% by weight, more preferably 20 to 60% by weight and even more preferably about 25% by weight.

The surfactant may comprise 5 to 80% by weight of the carrier medium; preferably 10 to 70% by weight, more preferably 20 to 60% by weight and even more preferably about 40% by weight.

The hydrophilic phase may comprise 5 to 50% by weight of the carrier medium, e.g. 10 to 50%; preferably 15 to 40% by weight, more preferably 20 to 35% by weight.

The active agent may be present in an amount by weight of up to about 20% by weight of the composition. The active agent is preferably present in an amount of 1 to 15% by weight of the composition, for example about 2 to 10%.

The difficultly soluble active agent preferably is a lipophilic drug, e.g. a cyclosporin or a macrolide. The term "difficultly soluble", as used herein, is understood to mean a solubility i,. water at 20° C. of less than 0.01% weight/volume.

Cyclosporins to which the present invention applies are any of those having pharmaceutical utility, e.g. as immunosuppressive agents, anti-parasitic agents and agents for the reversal of multi-drug resistance, as known and described in the art, in particular Cyclosporin A (also known as and referred to hereinafter as Ciclosporin), Cyclosporin G, [0-(2-hydroxyethyl)-(D)Ser]$^8$-Ciclosporin, and [3'-deshydroxy-3'-keto-MeBmt]$^1$-[Val]$^2$-Ciclosporin. Ciclosporin is preferred.

The term "macrolide" as used herein, refers to a macrocyclic lactone, for example a compound having a 12-membered or larger lactone ring. Of particular interest are the "lactam macrolides", i.e., macrocyclic compounds having a lactam (amide) bond in the macrocycle in addition to a lactone (ester) bond, for example the lactam macrolides produced by microorganisms of the genus Streptomyces such as rapamycin, ascomycin, and FK-506, and their numerous derivatives and analogues. Such lactam macrolides have been shown to have interesting pharmaceutical properties, particularly immunosuppressive and anti-inflammatory properties.

Rapamycin is an immunosuppressive lactam macrolide that is produced by *Streptomyces hygroscopicus*. The structure of rapamycin is given in Kesseler, H., et al.; 1993; *Helv. Chim. Acta;* 76: 117. The structure is depicted in Formula A:

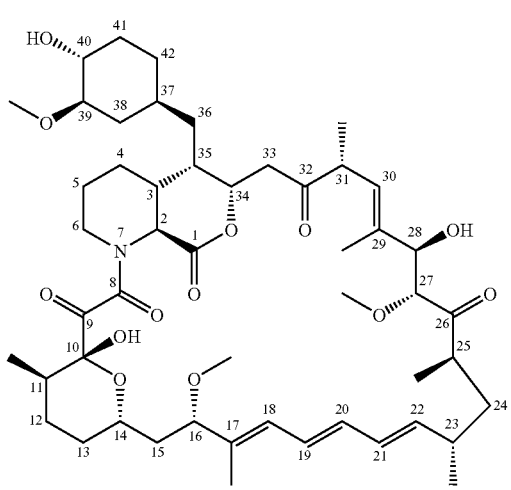

(A)

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. (There have been various numbering schemes proposed for rapamycin. To avoid confusion, when specific rapamycin derivatives are named herein, the names are given with reference to rapamycin using the numbering scheme of formula A.) Rapamycin is an extremely potent immunosuppressant and has also been shown to have antitumor and antifungal activity. Its utility as a pharmaceutical, however, is restricted by its very low and variable bioavailability as well as its high toxicity. Moreover, rapamycin is highly insoluble, making it difficult to formulate stable galenic compositions. Numerous derivatives of rapamycin are known. Certain 16-O-substituted rapamycins are disclosed in WO 94/02136, the contents of which are incorporated herein by reference. 40-O-substituted rapamycins are described in, e.g., in U.S. Pat. No. 5,258,389 and WO 94/09010 (O-aryl and O-alkyl rapamycins); WO 92/05179 (carboxylic acid esters), U.S. Pat. No. 5,118,677 (amide esters), U.S. Pat. No. 5,118,678 (carbamates), U.S. Pat. No. 5,100,883 (fluorinated esters), U.S. Pat. No. 5,151,413 (acetals), U.S. Pat. No. 5,120,842 (silyl ethers), WO 93/11130 (methylene rapamycin and derivatives), WO 94/02136 (methoxy derivatives), WO 94/02385 and WO 95/14023 (alkenyl derivatives) all of which are incorporated herein by reference. 32-O-dihydro or substituted rapamycin are described, e.g., in U.S. Pat. No. 5,256,790, incorporated herein by reference.

Rapamycin and its structurally similar analogues and derivatives are termed collectively as "rapamycins".

Ascomycins, of which FK-506 and ascomycin are the best known, comprise another class of lactam macrolides, many of which have potent immunosuppressive and anti-inflammatory activity. FK506 is a lactam macrolide immunosuppressant that is produced by *Streptomyces tsukubaensis* No 9993. The structure of FK506 is given in the appendix to the Merck Index, 11th ed. (1989) as item A5. Ascomycin is described, e.g., in U.S. Pat. No. 3,244,592. Many derivatives of ascomycin and FK-506 have been synthesized, including halogenated derivatives such as 33-epi-chloro-33-desoxy-ascomycin described in EP 427 680. Ascomycin, FK-506 and their structurally similar analogues and derivatives are termed collectively "ascomycins".

The macrolide may, therefore, be rapamycin or an O-substituted derivative in which the hydroxyl group on the cyclohexyl ring of rapamycin is replaced by —OR$_1$ in which R$_1$ is hydroxyalkyl, hydroalkoxyalkyl, acylaminoalkyl and aminoalkyl; for example 40-O-(2-hydroxy)ethyl-rapamycin, 40-O-(3-hydroxy)propyl-rapamycin, 40-O-[2-(2-hydroxy)ethoxy]ethyl-rapamycin and 40-O-(2-acetaminoethyl)-rapamycin.

A preferred compound is 40-0-(2-hydroxy)ethyl rapamycin as disclosed in WO 94/09010.

Examples of compounds of the FK 506 class are those mentioned above. They include for example FK 506, ascomycin and other naturally occurring compounds. They include also synthetic analogues.

A preferred compound of the FK 506 class is disclosed in EP 427 680, e.g. Example 66a also known as 33-epi-chloro-33-desoxy-ascomycin. Other preferred compounds are disclosed in EP 465 426, and in EP 569 337, e.g. the compound of Example 71 in EP 569 337.

The hydrophilic phase component comprises dimethylisosorbide and/or a lower alkyl alkanoic ester. The term lower alkyl will be understood to include C$_1$ to C$_4$, for example ethyl. The term alkanoic ester will be understood to include acetate and propionate. Ethyl acetate is preferred. Ethyl acetate has a solubility in water of 8.5 g per 100 ml at room temperature. Preferably the lower alkyl alkanoic esters have a solubility in water of from about 1 to about 30 g/100 ml at room temperature.

The hydrophilic phase may also comprise a co-component which may be selected from Transcutol (which has the formula C$_2$H$_5$—[O—(CH$_2$)$_2$]$_2$—OH), Glycofurol (also known as tetrahydrofurfuryl alcohol polyethylene glycol ether) and 1,2-propylene glycol. The hydrophilic phase may include further hydrophilic co-components, for example lower alkanols such as ethanol. These co-components will generally be present in partial replacement of other components of the hydrophilic phase. While the use of ethanol in the compositions is not essential, it has been found to be of particular advantage when the compositions are to be manufactured in soft gelatine, encapsulated form. This is because storage characteristics are improved, in particular the risk of active agent precipitation following encapsulation procedures is reduced. Thus the shelf life stability may be extended by employing ethanol or some other such co-component as an additional ingredient of the hydrophilic phase. The ethanol may comprise 0 to 60% by weight of the hydrophilic phase; preferably 20 to about 55% by weight and more preferably about 40 to 50% by weight. Small quantities of liquid polyethylene glycols may also be included in the hydrophilic phase.

Dimethylisosorbide is also known as 3,6-dianhydro-2,5-di-O-methyl-D-glucitole. It is available under the trade name Arlasolve DMI from the company ICI Americas Inc. It has the following physico-chemical properties:

| | |
|---|---|
| Boiling Point | approx. 234° C. |
| Density 25° C. | 1.164 |
| Refractive Index | 1.467 |
| Viscosity 25° C. | approx. 5 mPa · s |
| Dielectric Constant | approx. 7 |

GB 2 222 770 A discloses a wide variety of lipophilic phase components suitable for use in the present invention. Preferred lipophilic phase components are medium chain fatty acid triglycerides, mixed mono-, di-, tri-glycerides, and transesterified ethoxylated vegetable oils.

Suitable medium chain fatty acid triglycerides are those known and commercially available under the trade names Captex, Myritol, Capmul, Captex, Neobee and Mazol; Miglyol 812 being the most preferred. Miglyol 812 is a fractionated coconut oil comprising caprylic-capric acid triglycerides and having a molecular weight=about 520 daltons. Fatty acid composition=$C_6$ max. about 3%, $C_8$ about 50 to 65%, $C_{10}$ about 30 to 45%, $C_{12}$ max 5%; acid no.=about 0.1; saponification no. about 330 to 345; iodine no.=max 1. Miglyol 812 is available from the Hüls company.

These triglycerides are described in Fiedler, H. P. "Lexikon der Hilfsstoffe für Pharmazie, Kosmetik und angrenzende Gebiete", Editio Cantor, D-7960 Aulendorf, 3rd revised and expanded edition (1989), the contents of which are hereby incorporated by reference.

Mixed mono-, di-, tri-glycerides preferably comprise mixtures of $C_{12-20}$ fatty acid mono-, di- and tri-glycerides, especially mixed $C_{16-18}$ fatty acid mono-, di- and triglycerides. The fatty acid component of the mixed mono-, di- and tri-glycerides may comprise both saturated and unsaturated fatty acid residues. Preferably however they are predominantly comprised of unsaturated fatty acid residues; in particular $C_{18}$ unsaturated fatty acid residues. Suitably the mixed mono-, di-, tri-glycerides comprise at least 60%, preferably at least 75%, more preferably at least 85% by weight of a $C_{18}$ unsaturated fatty acid (for example linolenic, linoleic and oleic acid) mono-, di- and tri-glycerides. Suitably the mixed mono-, di-, tri-glycerides comprise less than 20%, for example about 15% or 10% by weight or less, saturated fatty acid (for example palmitic and stearic acid) mono-, di- and tri-glycerides.

Mixed mono-, di-, tri-glycerides are preferably predominantly comprised of mono- and di-glycerides; for example mono- and di-glycerides comprise at least 50%, more preferably at least 70% based on the total weight of the lipophilic phase. More preferably, the mono- and di-glycerides comprise at least 75% (for example about 80% or 85% by weight of the lipophilic phase.

Preferably monoglycerides comprise from about 25 to about 50%, based on the total weight of the lipophilic phase, of the mixed mono-, di-, tri-glycerides. More preferably from about 30 to about 40% (for example 35 to 40%) monoglycerides are present.

Preferably diglycerides comprise from about 30 to about 60%, based on the total weight of the lipophilic phase, of the mixed mono-, di-, tri-glycerides. More preferably from about 40 to about 55% (for example 48 to 50%) diglycerides are present.

Triglycerides suitably comprise at least 5% but less than about 25%, based on the total weight of the lipophilic phase, of the mixed mono-, di-, tri-glycerides. More preferably from about 7.5 to about 15% (for example from about 9 to 12%) triglycerides are present.

Mixed mono-, di-, tri-glycerides may be prepared by admixture of individual mono-, di- or tri-glycerides in appropriate relative proportion. Conveniently however they comprise transesterification products of vegetable oils, for example almond oil, ground nut oil, olive oil, peach oil, palm oil or, preferably, corn oil, sunflower oil or safflower oil and most preferably corn oil, with glycerol.

Such transesterification products are generally obtained as described in GB 2 257 359 and/or WO 94/09211 the contents of which are incorporated herein by reference.

Preferably some of the glycerol is first removed to give a "substantially glycerol free batch" when soft gelatine capsules are to be made.

Purified trans-esterification products of corn oil and glycerol provide particularly suitable mixed mono-, di-, and tri-glyceride hereinafter referred to as "refined oil" and produced according to the description of GB 2 257 359 and/or WO 94/09211.

The lipophilic phase may alternatively comprise e.g. a pharmaceutically acceptable oil, preferably with an unsaturated component such as a vegetable oil or fish oil.

The lipophilic phase may alternatively comprise suitable transesterified ethoxylated vegetable oils such as those obtained by reacting various natural vegetable oils (for example, maize oil, kernel oil, almond oil, ground nut oil, olive oil, soybean oil, sunflower oil, safflower oil and palm oil, or mixtures thereof) with polyethylene glycols that have an average molecular weight of from 200 to 800, in the presence of an appropriate catalyst. These procedures are known and an example is described in U.S. Pat. No. 3,288,824. Transesterified ethoxylated corn oil is particularly preferred.

Transesterified ethoxylated vegetable oils are known and are commercially available under the trade name LABRAFIL (H. Fiedler, loc cit, vol 2, page 707). Examples are LABRAFIL M 2125 CS (obtained from corn oil and having an acid number of less than about 2, a saponification number of 155 to 175, an HLB value of 3 to 4, and an iodine number of 90 to 110), and LABRAFIL M 1944 CS (obtained from kernel oil and having an acid number of about 2, a saponification number of 145 to 175 and an iodine number of 60 to 90). LABRAFIL M 2130 CS (which is a transesterification product of a $C_{12-18}$ glyceride and polyethylene glycol and which has a melting point of about 35 to 40° C., an acid number of less than about 2, a saponification number 185 to 200 and an iodine number of less than about 3) may also be used. The preferred transesterified ethoxylated vegetable oil is LABRAFIL M 2125 CS which can be obtained, for example, from Gattefossé, Saint-Priest Cedex, France.

Examples of suitable surfactants for use in this invention are:
  i) reaction products of a natural or hydrogenated castor oil and ethylene oxide. The natural or hydrogenated castor oil may be reacted with ethylene oxide in a molar ratio of from about 1:35 to about 1:60, with optional removal of the polyethyleneglycol component from the products. Various such surfactants are commercially available. The polyethyleneglycol-hydrogenated castor oils available under the trade name CREMOPHOR are especially suitable. Particularly suitable are CREMOPHOR RH 40, which has a saponification number of about 50 to 60, an acid number less than about 1, a water content (Fischer) less than about 2%, an $n_D^{60}$ of about 1.453 to 1.457 and an HLB of about 14 to 16; and CREMOPHOR RH 60, which has a saponification number, of about, 40 to 50, an acid number less than about 1, an iodine number of less than about 1, a water content (Fischer) of about 4.5 to 5.5%, an $n_D^{25}$ of about 1.453 to 1.457 and an HLB of about 15 to 17. An especially preferred product of this class is CREMOPHOR RH40. Also suitable are polyethyleneglycol castor oils such as that available under the trade name CREMOPHOR EL, which has a molecular weight (by steam osmometry) of about 1630, a saponification number of about 65 to 70, an acid number of about 2, an iodine number of about 28 to 32 and an $n_D^{25}$ of about 1.471.

Similar or identical products which may also be used are available under the trade names NIKKOL (e.g. NIKKOL HCO-40 and HCO-60), MAPEG (e.g. MAPEG CO-40h), INCROCAS (e.g. INCROCAS 40), and TAGAT (for example polyoxyethylene-glycerol-fatty acid esters e.g. TAGAT RH 40; and TAGAT TO, a polyoxyethylene-glycerol-trioleate having a HLB value of 11.3; TAGAT TO is preferred). These surfactants are further described in Fiedler loc. cit.

ii) Polyoxyethylene-sorbitan-fatty acid esters, for example mono- and tri-lauryl, palmityl, stearyl and oleyl esters of the type known and commercially available under the trade name TWEEN (Fiedler, loc.cit. p. 1300–1304) including the products TWEEN
20 [polyoxyethylene(20)sorbitanmonolaurate],
21 [polyoxyethylene(4)sorbitanmonolaurate],
40 [polyoxyethylene(20)sorbitanmonopalmitate],
60 [polyoxyethylene(20)sorbitanmonostearate],
65 [polyoxyethylene(20)sorbitantristearate],
80 [polyoxyethylene(20)sorbitanmonooleate],
81 [polyoxyethylene(5)sorbitanmonooleate],
85 [polyoxyethylene(20)sorbitantrioleate].
Especially preferred products of this class are TWEEN 40 and TWEEN 80.

iii) Polyoxyethylene fatty acid esters, for example polyoxyethylene stearic acid esters of the type known and commercially available under the trade name MYRJ (Fiedler, loc. cit., 2, p.834–835). An especially preferred product of this class is MYRJ 52 having a $D^{25}$ of about 1.1., a melting point of about 40 to 44° C., an HLB value of about 16.9., an acid value of about 0 to 1 and a saponification no. of about 25 to 35.

iv) Polyoxyethylene-polyoxypropylene co-polymers and block co-polymers, for example of the type known and commercially available under the trade names PLURONIC, EMKALYX and POLOXAMER (Fiedler, loc. cit., 2, p. 959). An especially preferred product of this class is PLURONIC F68, having a melting point of about 52° C. and a molecular weight of about 6800 to 8975. A further preferred product of this class is POLOXAMER 188.

v) Dioctylsulfosuccinate or di-[2-ethylhexyl]-succinate (Fiedler, loc. cit., 1, p. 107–108).

vi) Phospholipids, in particular lecithins (Fiedler, loc. cit., 2, p. 943–944). Suitable lecithins include, in particular, soya bean lecithins.

vii) Propylene glycol mono- and di-fatty acid esters such as propylene glycol dicaprylate (also known and commercially available under the trade name MIGLYOL 840), propylene glycol dilaurate, propylene glycol hydroxystearate, propylene glycol isostearate, propylene glycol laurate, propylene glycol ricinoleate, propylene glycol stearate and so forth (Fiedler, loc. cit., 2, p. 808–809).

The surfactant selected preferably has a hydrophilic-lipophilic balance (HLB) of at least 10, for example Cremophor.

Preferably the relative proportion of hydrophilic phase component(s), the lipophilic phase and the surfactant lie within the "microemulsion" region on a standard three way plot. The compositions thus obtained are microemulsion preconcentrates of high stability that are capable, on addition to water, of providing microemulsions having an average particle size of <1,500 Å (150 nm).

The microemulsion preconcentrate compositions, e.g. those in the examples hereinafter, may show good stability characteristics as indicated by standard stability trials, for example having a shelf life stability of up to one, two or three years, and even longer. The microemulsion preconcentrate compositions of this invention produce stable microemulsions, e.g. for up to one day or longer.

The pharmaceutical composition may also include further additives or ingredients, for example antioxidants (such as ascorbyl palmitate, butyl hydroxy anisole (BHA), butyl hydroxy toluene (BHT) and tocopherols) and/or preserving agents. These additives or ingredients may comprise about 0.05 to 1% by weight of the total weight of the composition. The pharmaceutical composition may also include sweetening or flavoring agents in an amount of up to about 2.5 or 5% by weight based on the total weight of the composition. Preferably the antioxidant is α-tocopherol (vitamin E).

The pharmaceutical compositions exhibit especially advantageous properties when administered orally; for example in terms of consistency and high level of bioavailability obtained in standard bioavailability trials, e.g. 2 to 4 times higher than emulsions. These trials are performed in animals e.g. rats or dogs or healthy volunteers using HPLC or a specific or nonspecific monoclonal kit to determine the level of the drug substance, e.g. macrolide in the blood. For example, the composition of Example 1 administered p.o. to dogs may give surprisingly high $C_{max}$ values as detected by ELISA using a specific monoclonal antibody.

Pharmacokinetic parameters, for example absorption and blood levels, also become surprisingly more predictable and problems in administration with erratic absorption may be eliminated or reduced. Additionally the pharmaceutical compositions are effective with tenside materials, for example bile salts, being present in the gastro-intestinal tract. That is, the pharmaceutical compositions are fully dispersible in aqueous systems comprising such natural tensides and thus capable of providing microemulsion systems in situ which are stable and do not exhibit precipitation of the active agent or other disruption of fine particulate structure. The function of the pharmaceutical compositions upon oral administration remain substantially independent of and/or unimpaired by the relative presence or absence of bile salts at any particular time or for any given individual.

The compositions of this invention reduce variability in inter- and intra-patient dose response.

In a further aspect the invention also provides a process for the production of a pharmaceutical composition as defined above, which process comprises bringing (1) the hydrophilic phase; (2) the lipophilic phase; and (3) the surfactant into intimate admixture, and adding the active agent, e.g. cyclosporin or the compound of the macrolide class. When required, the composition may be compounded into unit dosage form, for example filling the composition into gelatine capsules.

Optionally further components or additives, in particular a hydrophilic phase co-component, for example ethanol, may be mixed with components (1), (2) and (3) or with or after addition of active agent.

The composition may be combined with water or an aqueous solvent medium such that a microemulsion is obtained.

The present applicants also contemplate microemulsion preconcentrate compositions which may be free of refined fish oil and/or ethanol and/or transesterified ethoxylated vegetable oil.

The present applicants have found that macrolides are unstable upon storage, for example 40-0-(2-hydroxy)ethyl rapamycin, and can undergo a variety of different degradation reactions. Upon storage, for example, of several days, one or more degradation products may be identified, e.g. using HPLC. Although degradation pathways have yet to be identified, the applicants believe that rupture of the macrolide lactone ring may occur.

The present applicants have identified as 40-0-(2-hydroxy)ethyl rapamycin-2,34-secoacid as a main degradation product of 40-0-(2-hydroxy)ethyl rapamycin. 40-0-(2-hydroxy)ethyl rapamycin-2,34-secoacid, referred to hereinafter as secoacid, has the following structure:

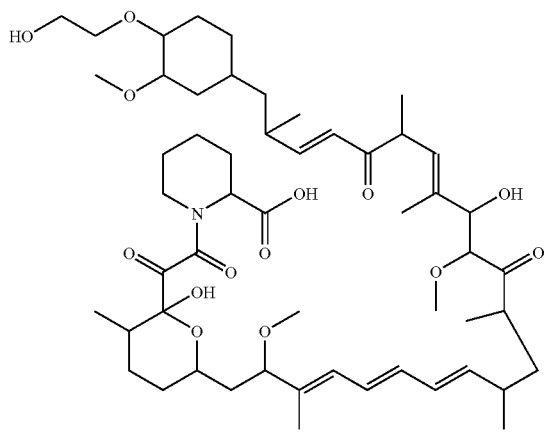

It has now been found that stable compositions containing macrolides may be obtained by formulating the macrolide in an acidic environment. Compositions are understood herein to be stable when the macrolide drug substance remains substantially intact after a period of days or weeks at room temperature (25° C.).

In another aspect, this invention provides a pharmaceutical composition comprising a macrolide and an acid.

The term macrolide has the meaning as described above.

Preferred macrolides have at least one moiety as follows

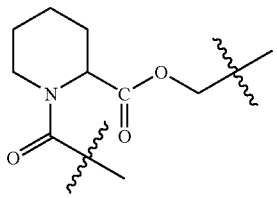

Examples are those mentioned above and are preferably rapamycin or 40-0-(2-hydroxy)ethyl rapamycin.

The acid may be lipid soluble and/or ethanol soluble. The acid may be for example a fatty acid, e.g. oleic acid. The acid may be a carboxylic acid, for example a mono-, di- or tri-carboxylic acid, and preferably a mono- or dicarboxylic acid. The acid may comprise one or more hydrophilic groups, e.g. hydroxy groups, and preferably one or two hydrophilic groups. Suitable acids for use in this invention include malonic acid, fumaric acid, maleic acid, D-malic acid, L-malic acid, citric acid, ascorbic acid, succinic acid, oxalic acid, benzoic acid or lactic acid or an acid with a similar pKa, e.g. 2–7. Preferred acids include malonic acid, oxalic acid, citric acid and lactic acid. Malonic acid is more preferred.

The preferred amount of acid may be determined by routine experimentation. The ratio by weight of macrolide to acid in the compositions of this invention may be up to 20:1, for example from 1:5 to 5:1, e.g. 1:1. The acid may be present in an amount of between 0.05% and 5% by weight of the composition.

The macrolide may be present in an amount of 1 to 15% by weight of the composition.

The type of pharmaceutical composition is not critical. It may be solid, but it is preferably liquid. The macrolide may, for example, be formulated into a microemulsion preconcentrate or emulsion preconcentrate as defined above, and combined with an amount of acid. The acid-stabilised composition may be administered enterally, e.g orally, e.g. as a capsule or drink solution, or parenterally, e.g. as an infusion concentrate. Oral administration is preferred.

In another aspect, this invention provides the use of an acid to stabilise a macrolide in a pharmaceutical composition.

In another aspect, this invention provides a method of stabilising a macrolide in a pharmaceutical composition, which method comprises mixing an acid with the macrolide.

This invention thus allows preparation of stable macrolide compositions. Good drug bioavailability and low variability in inter- and intra-patient dose response may be obtained.

The utility of all the pharmaceutical compositions of the present invention may be observed in standard clinical tests in, for example, known indications of active agent dosages giving equivalent blood levels of active agent; for example using dosages in the range of 2.5 mg to 1000 mg of active agent per day for a 75 kilogram mammal, e.g. adult and in standard animal models. The increased bioavailability of the active agent provided by the compositions may be observed in standard animal tests and in clinical trials, e.g. as described above.

The optimal dosage of active agent to be administered to a particular patient must be considered carefully as individual response to and metabolism of the macrolide compound, e.g. rapamycin, may vary. It may be advisable to monitor the blood serum levels of the active agent by radioimmunoassay, monoclonal antibody assay, or other appropriate conventional means. Dosages of a macrolide will generally range from 1 to 1000 mg per day, e.g. 2.5 mg to 1000 mg per day for a 75 kilogram adult, preferably 25 mg to 500 mg, with the optimal dosage being approximately 50 to 100 mg per day. Satisfactory results are obtained by administering about 75 mg per day for example in the form of two capsules, one containing 50 mg and one containing 25 mg; or three capsules each containing 25 mg. Cyclosporin dosages may be 25 to 1000 mg per day (preferably 50 mg to 500 mg) and the FK 506 dosage may be 2.5 mg to 1000 mg per day (preferably 10 mg to 250 mg). A daily dosage of between 0.5 and 5 mg/kg body weight/day is indicated for administration of 40-0-(2-hydroxy)ethyl rapamycin.

The pharmaceutical compositions are preferably compounded in unit dosage form, for example by filling them into orally administrable capsule shells. The capsule shells may be soft or hard gelatine capsule shells. Where the pharmaceutical composition is in unit dosage form, each unit dosage will suitably contain between 10 and 100 mg of the active agent, more preferably between 10 and 50 mg; for example 15, 20, 25, or 50 mg. Such unit dosage forms are suitable for administration 1 to 5 times daily depending upon the particular purpose of therapy, the phase of therapy and the like.

However, if desired, the pharmaceutical compositions may be in drink solution form and may include water or any other aqueous system, to provide microemulsion systems suitable for drinking.

The pharmaceutical compositions are particularly useful for treatment and prevention of the conditions disclosed at pages 40 and 41 in EP 427 680, and at pages 5 and 6 in PCT/EP93/02604, the contents of which applications are incorporated herein by reference.

The pharmaceutical compositions are particularly useful for:

a) treatment and prevention of organ or tissue transplant rejection, for example for the treatment of the recipients of heart, lung, combined heart-lung, liver, kidney, pancreatic, skin or corneal transplants. The pharmaceutical compositions are also indicated for the prevention of graft-versus-host disease, such as sometimes occurs following bone marrow transplantation;

b) treatment and prevention of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases; and c) treatment of multi-drug resistance (MDR).

The macrolide active agents also exhibit anti-tumour and antifungal activity and hence the pharmaceutical compositions can be used as anti-tumour and anti-fungal agents.

The contents of all the references referred to above especially the exemplified compounds are incorporated herein by reference, and each of the exemplified compounds may be used as a macrolide in the examples listed below.

EXAMPLES

Following is a description by way of example only of compositions of this invention. Unless otherwise indicated, components are shown in % by weight based on each composition.

Examples 1 to 20

Following is a description by way of example only of microemulsion preconcentrate compositions of this invention in which the hydrophilic phase comprises DMI or ethyl acetate.

Examples 1 and 2 illustrate compositions in unit dosage form, suitable for use, for example in the prevention of transplant rejection or for the treatment of autoimmune disease, on administration of from 1 to 5 unit dosages/day. The examples are described with particular reference to Ciclosporin but equivalent compositions may be obtained employing any macrolide or other active agent.

Example 1

Preparation of oral unit dosage forms

| COMPONENT | QUANTITY (mg/capsule) |
|---|---|
| Cyclosporin, e.g. Ciclosporin | 100 |
| 1) Dimethylisosorbide | 100–200, e.g. 150 |
| 2) refined corn oil or Labrafil M2125CS | 100–500, e.g. 320 |
| 3) Cremophor RH40 | 100–500, e.g. 380 |
| 4) Ethanol | 10–100, e.g. 50 |
| | Total 1,000 (by selecting appropriate amounts from ranges) |

A batch of 1000 capsules is made.

The cyclosporin is dissolved in (1) with stirring at room temperature and (2) and (3) are added to the obtained solution again with stirring. 0.5 ml portions of the obtained mixture are filled into size 1 hard gelatine capsules and sealed, e.g. using the Quali-Seal technique, or into soft gelatine capsules.

Compositions comprising 50 and 100 mg Ciclosporin, are prepared analogously employing the following indicated ingredients in the indicated amounts.

In this Example, refined oil="refined glycerol-transesterified corn oil", substantially glycerol free, as described in GB 2 257 359 and WO 94/09211.

Example 2

Preparation of an Oral Drink Solution

The composition is made in analogous manner as in Example 1 on the 5 liter scale if desired replacing the ethanol with an equivalent amount of further dimethylisosorbide.

Examples 3 to 19

Cyclosporin A compositions are prepared using as lipophilic phase:

Miglyol 812 (from the Hüls company) in Examples 3 to 9;

Cornoil glyceride (refined corn oil mono-, di-, and triglycerides) in Examples 10 to 17; and Labrafil 2125 CS (from the Gattefossé company) in Examples 18 and 19.

Dimethylisosorbide is abbreviated as DMI in the following examples.

The carrier medium is prepared by mixing the components one with another. The cyclosporin A is then dissolved in the carrier medium by stirring.

FIGS. 1 to 5 represent three-way plots for relative concentrations of each of the hydrophilic, lipophilic and surfactant components. Relative concentration of the DMI increases from 0% at the right hand margin of the plot to 100% at the lower left hand corner as indicated by the arrow. Relative concentration of the surfactant, abbreviated to S in FIGS. 1 to 5, increases from the base line of the plot to 100% at the apex as indicated by the arrow. Relative concentration of the lipophilic phase increases from 0% along the left hand margin of the plot to 100% at the lower right hand corner as indicated by the arrow. Lines within the plot represent increments of 10%, from 0% at each margin to 100% at the respective apex opposite.

Thus a theoretical composition comprising 50% of lipophilic phase and 50% of DMI only, is designated at the mid-point of the base line of the plot.

Figure 2:
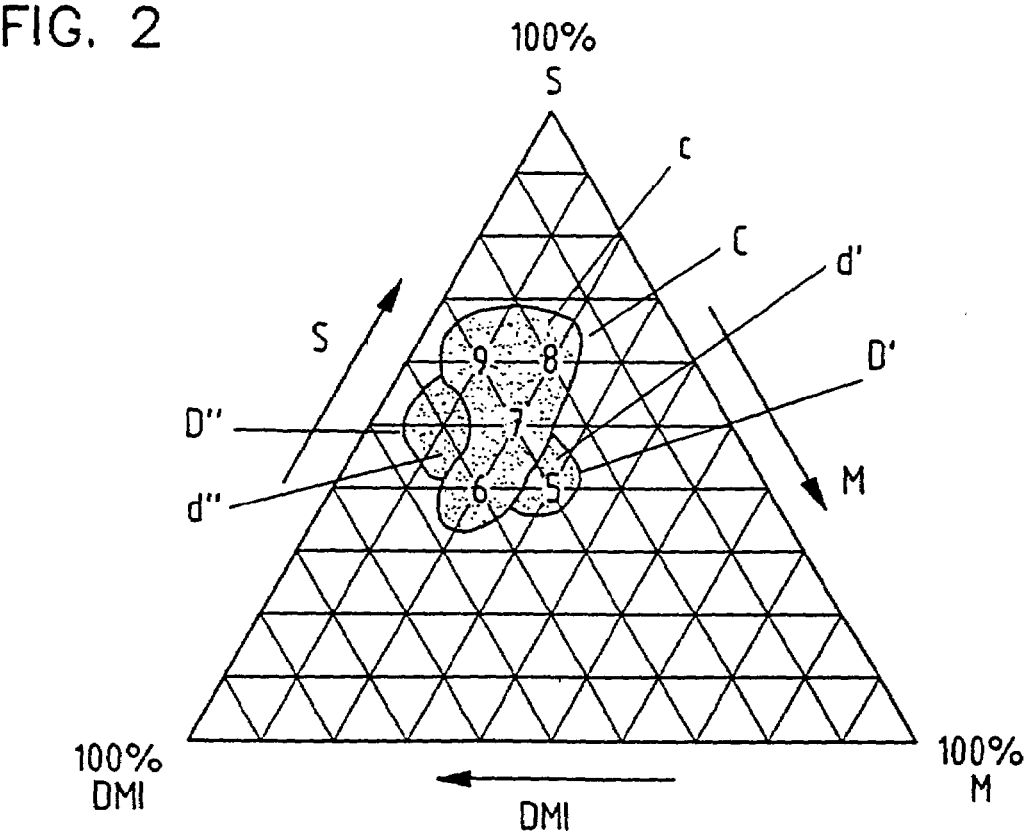
Figure 3:
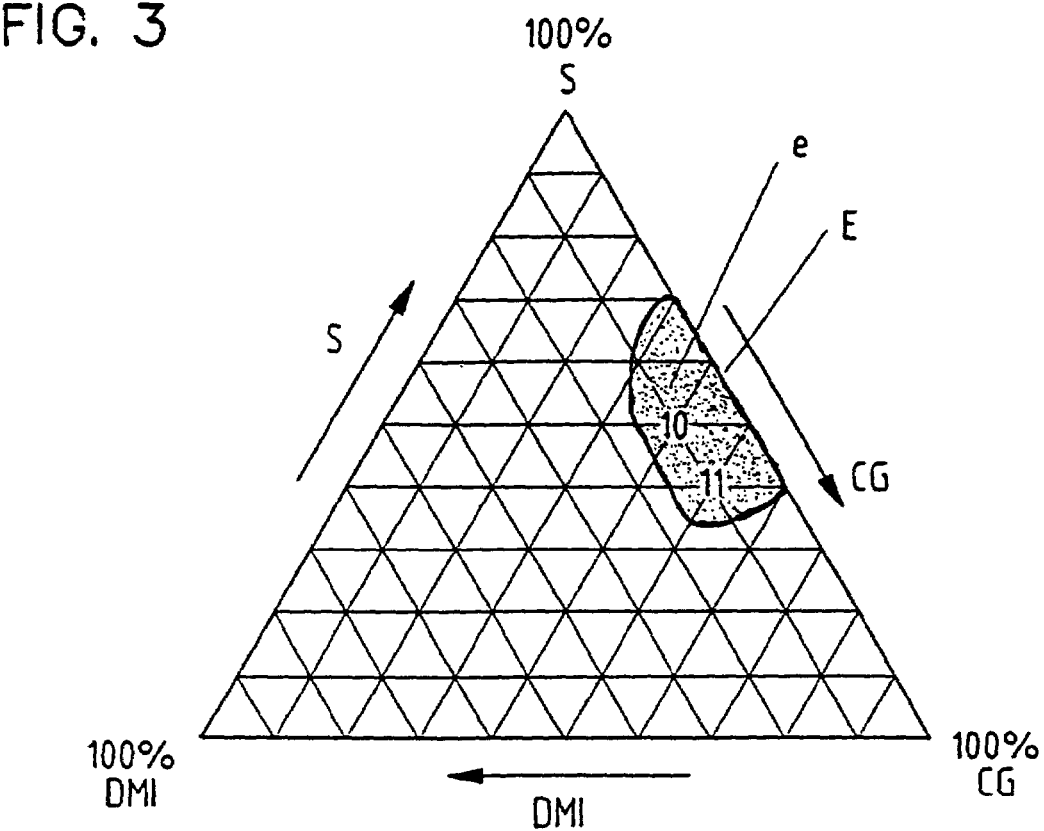
Figure 4:
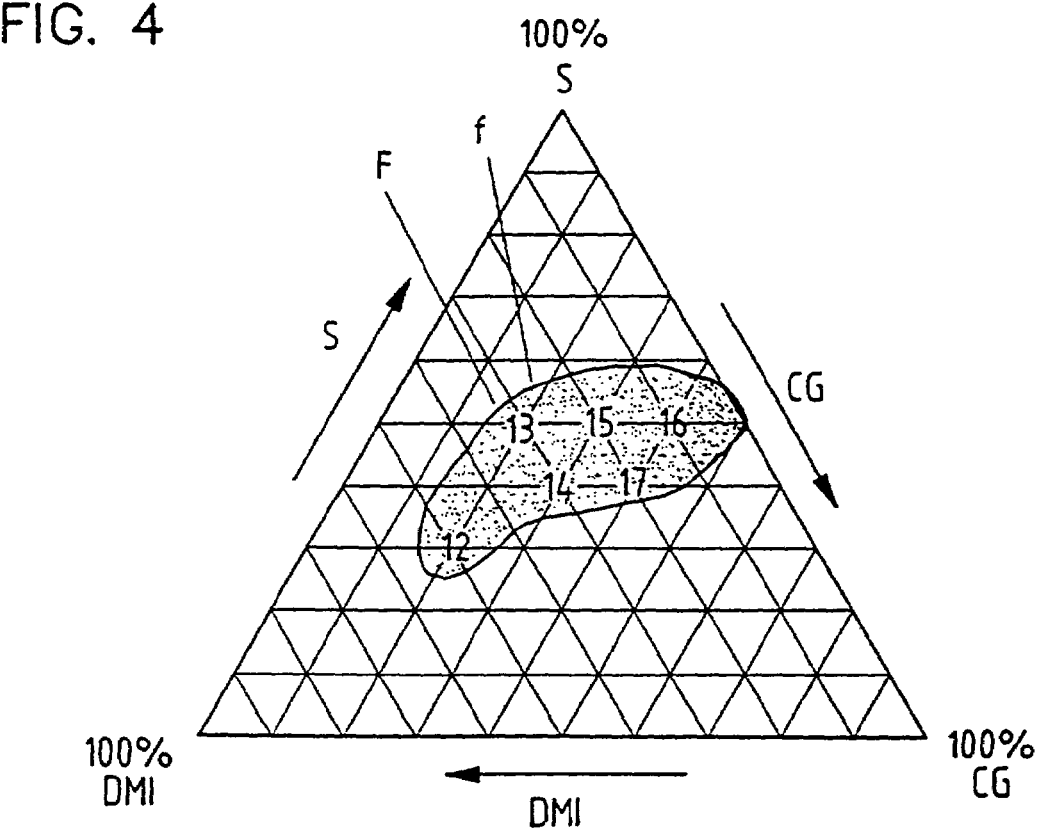
Figure 5:
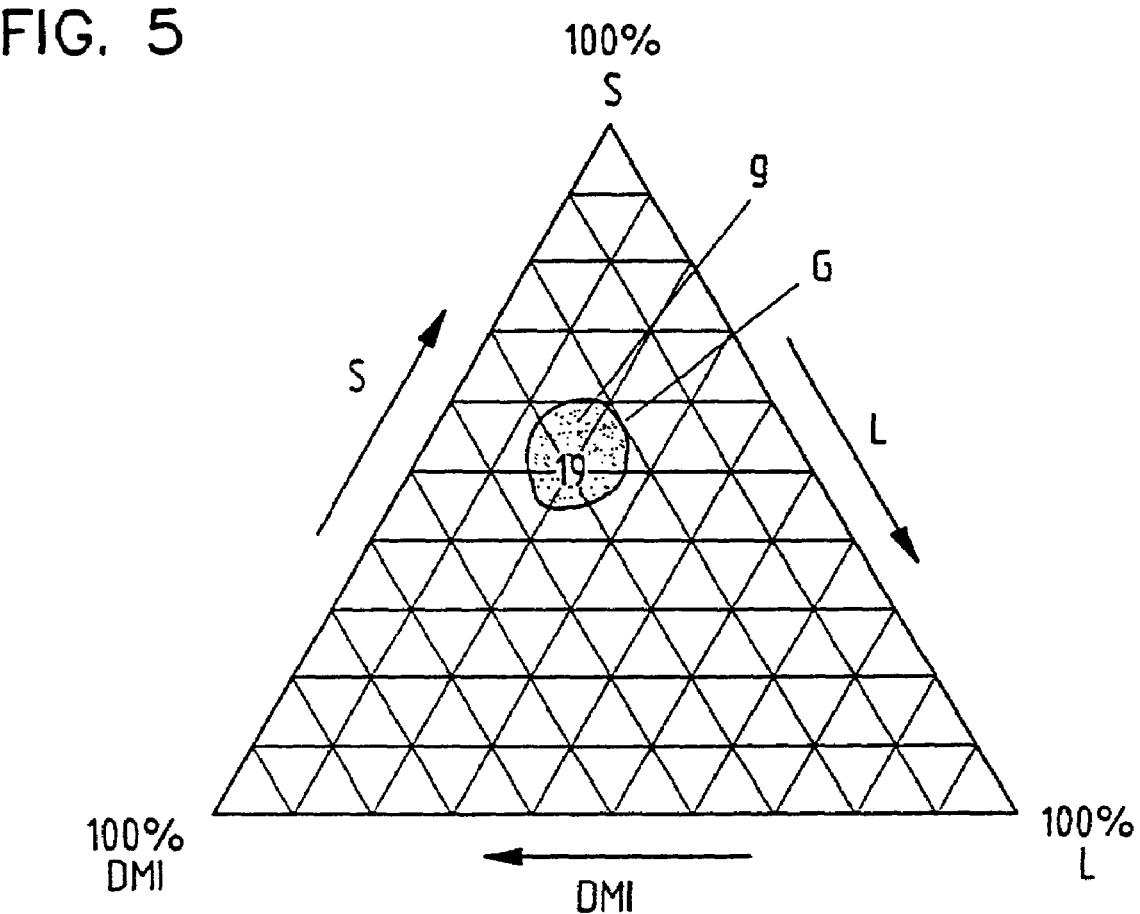

For preferred compositions of this invention, the relative proportions of the main carrier medium components lie within areas a and b defined respectively by lines A and B in FIG. 1; areas c, d' and d" defined respectively by lines C, D' and D" in FIG. 2; area e defined by line E in FIG. 3; area f defined by line F in FIG. 4; and area g defined by line G in FIG. 5.

In FIGS. 1 and 2, Miglyol 812 is abbreviated to M. In FIGS. 3 and 4, corn oil glyceride is abbreviated to CG. In FIG. 5, Labrafil 2125 CS is abbreviated to L.

Particle size measurements are made at 20° C. at a dilution of 60 μl composition in 1 ml water by photon correlation spectroscopy using, for example a Malvern Zeta-Sizer No. 3 from Malvern Instruments.

Examples 3 to 9

The following cyclosporin A compositions are made up using Miglyol 812. Ethanol is present in an amount of 10% by weight in the compositions of Examples 3 and 4.

| Example: | 3 | 4 |
|---|---|---|
| Cremophor RH 40 | 48 | 40 |
| Miglyol 812 | 24 | 32 |
| DMI | 8 | 8 |
| Ethanol abs. | 10 | 10 |
| Ciclosporin | 10 | 10 |

No phase separation is observed for compositions 3 and 4 which are clear. On dilution with water, the composition of Example 3 remains clear at 1:1 and at 1:10 dilution by volume. The composition of Example 4 is opalescent on dilution with water at 1:1 and at 1:10 (1 part composition, 10 parts by volume water). FIG. 1 shows a three-way plot for compositions 3 (area a) and 4 (area b).

| Example: | 5 | 6 | 7 | 8 | 9 |
|---|---|---|---|---|---|
| Cremophor RH 40 | 36 | 36 | 45 | 54 | 54 |
| Miglyol 812 | 27 | 18 | 18 | 18 | 9 |
| DMI | 27 | 36 | 27 | 18 | 27 |
| Ciclosporin | 10 | 10 | 10 | 10 | 10 |

No phase separation is observed for any of compositions 5 to 9 which are clear. On dilution with water, the compositions of Examples 5 to 9 remain clear at 1:1 and at 1:10 dilution. FIG. 2 represents a three-way plot for each of compositions 5 to 9 (areas c, d' and d").

Examples 10 to 17

Cyclosporin A compositions of Examples 10 to 17 are prepared using cornoil glyceride. Ethanol is present in an amount of 10% by weight in the compositions of Examples 10 and 11.

| Example | 10 | 11 |
|---|---|---|
| Cremophor RH 40 | 40 | 32 |
| Cornoil glyceride | 32 | 40 |
| DMI | 8 | 8 |
| Ethanol abs. | 10 | 10 |
| Ciclosporin | 10 | 10 |

No phase separation is observed for compositions 10 and 11 which are clear. On dilution with water, the compositions of Examples 10 and 11 remain clear at 1:1 and at 1:10 dilution by volume (1 part composition, 10 parts water). FIG. 3 represents a three way plot for compositions 10 and 11 (area e).

| Example: | 12 | 13 | 14 | 15 | 16 | 17 |
|---|---|---|---|---|---|---|
| Cremophor RH 40 | 27 | 45 | 36 | 45 | 45 | 36 |
| Cornoil glyceride | 18 | 18 | 27 | 27 | 36 | 36 |
| DMI | 45 | 27 | 27 | 18 | 9 | 18 |
| Ciclosporin | 10 | 10 | 10 | 10 | 10 | 10 |

No phase separation is observed for any of compositions 12 to 17 which are clear. On dilution with water, the compositions of Examples 12 to 17 remain clear at 1:10 dilution by volume (1 part composition, 10 parts water). On dilution with water at a ratio of 1:1, the compositions of Examples 12, 13, 14, 15 and 17 remained clear, and that of Example 16 appears opalescent.

FIG. 4 represents a three way plot for compositions 12 to 17 (area f).

Examples 18 and 19

Cyclosporin A compositions of Examples 18 and 19 are prepared using Labrafil 2125 CS as lipophilic phase.

| Example: | 18 | 19 |
|---|---|---|
| Cremophor RH 40 | 27 | 45 |
| Labrafil 2125 CS | 18 | 18 |
| DMI | 45 | 27 |
| Ciclosporin | 10 | 10 |

No phase separation is observed for composition 18 or 19 which are clear. On dilution with water, the composition of Example 19 remains clear at 1:1 and at 1:10 dilution (1 part composition, 10 parts water by volume). On dilution with water at a ratio of 1:1 and 1:10, composition 18 appears opalescent. FIG. 5 represents a three way plot for composition 19 (area g).

For the compositions 3 to 19, particle size distribution is determined. The maximum particle size is below 70 nm in all compositions. The z-average mean particle size lies between 22.0 and 32.6 nm. The Polydispersity index lies between 0.076 and 1.164.

Examples 20 to 24

Microemulsion preconcentrates are prepared using ethyl acetate as hydrophilic phase. The compositions are diluted with water, at 1:1 dilution and 1 part composition:10 parts water, to form microemulsions.

| Example: | 20 | 21 | 22 | 23 | 24 |
|---|---|---|---|---|---|
| Cremophor RH 40 | 40 | 45 | 45 | 54 | 48 |
| Cornoil glyceride | 24 | 27 | | | |
| Labrafil M2125 CS | | | 27 | | |
| Miglyol 812 | | | | 18 | 24 |
| Ethylacetate | 16 | 18 | 18 | 18 | 8 |
| Ethanol | 10 | | | | 10 |
| Ciclosporin A | 10 | 10 | 10 | 10 | 10 |

-continued

| Example: | 20 | 21 | 22 | 23 | 24 |
|---|---|---|---|---|---|
| Dilution with water | | | | | |
| 1:1 | clear | clear | clear | clear | clear |
| 1:10 | clear | clear | clear | clear | clear |
| droplet size | | | | | |
| z average mean | 26.9 nm | 23.7 nm | 29.3 nm | 27.1 | 33.2 |
| Polydispersity | 0.08 | 0.089 | 0.110 | 0.152 | 0.111 |

On visual inspection after dilution, each of the compositions 20 to 24 forms a clear and stable microemulsion.

Storage

The undiluted compositions of Examples 1 to 24 remain stable, i.e. no precipitation or crystallisation is observed, for at least one month at room temperature. After storage undiluted at room temperature for two months, the compositions of Examples 5, 6, 7, 12 and 18 remain clear.

Examples 25 to 27

Microemulsion preconcentrates are prepared and stored at room temperature for 12 months:

| Example 25 | Amount % by weight |
|---|---|
| Cremophor RH40 | 24 |
| Cornoil glyceride | 48 |
| DMI | 8 |
| ethanol abs | 10 |
| Cyclosporin A | 10 |

No precipitation or crystallisation is observed after 12 months storage.

| Example 26 | Amount % by weight |
|---|---|
| Cremophor RH40 | 27 |
| Cornoil glyceride | 54 |
| DMI | 9 |
| Cyclosporin A | 10 |

No precipitation or crystallisation is observed after 12 months storage.

| Example 27 | Amount % by weight |
|---|---|
| Cremophor RH40 | 27 |
| Cornoil glyceride | 45 |
| DMI | 18 |
| Cyclosporin A | 10 |

No precipitation or crystallisation is observed after 12 months storage.

Cyclosporin A may be replaced with another cyclosporin, or with a macrolide, e.g. rapamycin, 40-0-(2-hydroxy)ethyl rapamycin, 33-epi-chloro-33-desoxy-ascomycin or the compound of Example 71 in EP 569 337 in any composition described in Examples 1 to 27.

Examples 28 to 32

Following is a description by way of example only of macrolide compositions stabilised by an acid.

Example 28

An active agent of the FK 506 class or rapamycin class e.g. 40-0-(2-hydroxy)ethyl rapamycin is made up into a microemulsion preconcentrate having the following composition by weight 2% active compound, 2% malonic acid, lactic acid or famonic acid, 44% Cremophor RH40 26.4% corn-oil mono-, di-, tri-glycerides, 17.6% 1,2 propylene glycol and 10% ethanol.

Stability tests over 3 months showed that a malonic acid composition contained 98% of active agent thereafter and without the malonic acid only 73%.

Examples 29 and 30

Microemulsion preconcentrates are prepared using 40-0-(2-hydroxy)ethyl rapamycin in Examples 29a and 29b, and rapamycin in Examples 30a and 30b as active agent. In Example 29, the active agent 40-0-(2-hydroxy)ethyl rapamycin is abbreviated to "active agent R".

Intact drug content and main degradation product are determined by HPLC with an analytical error of +/−2%.

| Composition | Example 29a active agent R | Example 29b active agent R malonic acid | Example 30a Rapamycin | Example 30b Rapamycin malonic acid |
|---|---|---|---|---|
| Cremophor RH 40 | 44.0% | 43.0% | 41.5% | 40.5% |
| Cornoil glyceride | 26.3% | 25.7% | 24.8% | 24.2% |
| Propylene glycol | 17.6% | 17.2% | 16.6% | 16.2% |
| Ethanol abs. | 10.0% | 10.0% | 15.0% | 15.0% |
| DL-α-Tocopherol | 0.1% | 0.1% | 0.1% | 0.1% |
| active agent R | 2.0% | 2.0% | — | — |
| Rapamycin | — | — | 2.0% | 2.0% |
| Malonic acid | — | 2.0% | — | 2.0% |
| Intact drug content and main degradation product (seco acid) expressed as percentages of amount (HPLC evaluation by external standardization) | | | | |
| 4 weeks at 25° C. | 86.0% (16.1%) | 99.5% (0.5%) | 83.5% (15.4%) | 98.4% (0.7%) |

Amount of main degradation product is shown in brackets. Main degradation product of rapamycin is referred to as secorapamycin.

The above examples demonstrate that malonic acid exhibits a pronounced stabilizing effect on the degradation of 40-0-(2-hydroxy)ethyl rapamycin and of rapamycin.

Example 31

The composition of Example 29a is mixed with malonic acid at concentrations between 0.05% and 5% by weight. A highly stabilising effect is observed with malonic acid in the concentration range 0.25 to 0.75% by weight of the composition.

Example 32

A concentrate for infusion is prepared using the following composition:

| | |
|---|---|
| 40-0-(2-hydroxy)ethyl rapamycin | 20 mg/ml |
| Cremophor EL | 600 mg/ml |
| citric acid | 10 mg/ml |
| ethanol | to 1 ml |

After 4 weeks storage at 25° C., an active ingredient assay of 99.6% is obtained. This demonstrates that citric acid has a stabilising effect on 40-0-(2-hydroxy)ethyl rapamycin.

In the above Examples 28 to 32 the active agent may replaced by 33-epichloro-33-desoxy-ascomycin or by the compound of Example 71 in EP 569 337.

The invention claimed is:

1. A microemulsion pre-concentrate comprising a difficultly soluble active agent wherein the active agent is a cyclosporin or a lactam macrolide, and a carrier medium comprising:
   1) a hydrophilic phase which comprises a lower alkyl alkanoic ester,
   2) a lipophilic phase, and
   3) a surfactant.

2. A microemulsion pre-concentrate as claimed in claim 1 wherein the active agent is selected from Cyclosporin A, rapamycin, 40-O-(2-hydroxy)ethyl rapamycin, 33-epichloro-33-desoxy-ascomycin, FK 506 or ascomycin.

3. A microemulsion pre-concentrate as claimed in claim 1 or 2 wherein the hydrophilic phase comprises ethyl acetate as lower alkyl alkanoic ester.

4. A microemulsion pre-concentrate as claimed in claim 1 or 2 for oral or parenteral administration.

* * * * *